(12) United States Patent
Oliver et al.

(10) Patent No.: US 6,800,476 B1
(45) Date of Patent: Oct. 5, 2004

(54) REGULATED EXPRESSION OF PKC AND/OR SRB1/PSA1 IN YEAST

(75) Inventors: Stephen Oliver, Cheshire (GB); Lubomira I. Stateva, Manchester (GB); Nianshu Zhang, Manchester (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/700,492

(22) PCT Filed: May 17, 1999

(86) PCT No.: PCT/GB99/01557

§ 371 (c)(1),
(2), (4) Date: Jan. 5, 2001

(87) PCT Pub. No.: WO99/60138

PCT Pub. Date: Nov. 25, 1999

(30) Foreign Application Priority Data

May 16, 1998 (GB) .............................................. 9810442

(51) Int. Cl.⁷ .............................. C12N 1/16; C12N 1/18
(52) U.S. Cl. .................... 435/255.1; 435/440; 435/471; 435/483; 435/243; 435/255.2; 435/259; 435/320.1; 536/23.1; 536/23.74; 536/24.1
(58) Field of Search ................................ 435/400, 471, 435/476, 477, 483, 243, 252.3, 254.1, 255.1, 255.2, 255.21, 255.5, 255.6, 255.7, 259, 260, 320.1; 536/22.1, 23.1, 23.74, 24.1

(56) References Cited

PUBLICATIONS

Everett et al. Pendred syndrome is caused by mutations in a putative sulphate transporter gene (PDS). Dec. 1997. Nature Genetics 17:411–422.*

Scott et al. The Pendred syndrome gene encodes a chloride–iodide transport protein. Apr. 1999. Nature Genetices 21:440–444.*

Alvarez, Pablo et al., "A New System for the Release of Heterologous Proteins from Yeast Based on Mutant Strains Deficient in Cell Integrity", Journal of Biotechnology 38 (1994), pp. 81–88.

Alvarez, Pablo et al., "Release of Virus–Like Particles by Osmotic Shock from a Mutant Strain of Yeast Deficient in Cell Integrity", Biotechnology Techniques, vol. 9, No. 6 (Jun. 1995), pp. 441–444.

Cid, Victor J. et al., "Molecular Basis of Cell Integrity and Morphogenesis in *Saccharomyces cerevisiae*", Microbiological Reviews, Sep. 1995, pp. 345–386.

Lyutskanov, Nikola et al., "Protein Extracts for Nutritional Purposes from Fragile Strains of *Saccharomyces cerevisiae*: Reduction of the Nucleic Acid Content and Applicability of the Protein Extracts", J. Basic Microbiol. 30 (1990) 7, pp. 523–528.

Stateva, Lubomira et al., "Protein Extracts for Nutritional Purposes from Fragile Strains of *Saccharomyces cerevisiae*: Construction of Strains and Conditions for Lysis", J. Basic Microbiol. 30 (1990) 7, pp. 535–540.

* cited by examiner

*Primary Examiner*—James Ketter
*Assistant Examiner*—David A. Lambertson
(74) *Attorney, Agent, or Firm*—Nixon & Vanderhye PC

(57) ABSTRACT

The present invention relates to yeast cells containing the SRB1/PSA1 gene and/or the PKC1 gene or functional derivatives thereof operatively linked to a heterologous inducible promoter and also to methods of regulating yeast cell lysis and flocculation and methods of fermentation using such yeast cells.

17 Claims, 7 Drawing Sheets

Met⁻

Met⁺

1-ZO123, Met⁻; 2-ZO123, Met⁺; 3-ZO125, Met⁻; 4-ZO125, Met⁺; 5-ZO123/SRB1.9e, ME⁻

Met⁻

Met⁺

REGULATED EXPRESSION OF PKC AND/OR SRB1/PSA1 IN YEAST

This is a 371 of PCT/GB99/01557, filed May 17, 1999, which claims priority from GB 9810442.5, filed May 16, 1998.

The present invention relates to genetically modified yeasts in which the expression of genes responsible for cell wall synthesis are modulated.

The yeast cell wall is a dynamic organelle responsible for a number of cellular functions, the most important being physical and osmotic protection, selective permeability, cell-cell recognition and adhesion during mating and flocculation.

The cell wall of the yeast *Saccharomyces cerevisiae* is composed of three components, β-glucan (a glucose polymer), mannoproteins and chitin (an N-acetylglucosamine polymer). The β-glucan component of the cell wall consists of two polymers: a large, linear β-1,3-glucan and a smaller, highly branched β-1,6-glucan moiety whereas the mannoproteins are a complex of proteins modified by the attachment, via N- and O-glycosidic bonds, of mannose-containing carbohydrate chains of different length and structure.

The yeast cell wall is a very rigid, highly complex structure which determines the shape of the yeast cell and enables it to be protected from and adjusted to its ever-changing environment. A growing number of genes have been shown to participate in the biosynthesis and assembly of the major cell wall components, some of them as part of well-defined signal transduction pathways. For instance, PKC1 (the yeast homologue of protein kinase C) regulates the biosynthesis and assembly of major cell wall components by a PKC1-mediated signal transduction pathway. PKC1, in conjunction with Rho1p, regulates β1–3 glucan synthetase Null mutants of PKC1 can only grow in the presence of osmotic stabilisers. Loss of PKC1 function results in a cell-cycle-specific osmotic stability defect.

A further gene relevant to the cell wall is the recently identified SRB1 (also known as PSA1 or VIG9) yeast gene which is essential for growth and encodes GDP-mannose pyrophosphorylase, an enzyme responsible for the production of a major substrate for all kinds of mannosylation reactions, including the biosynthesis of cell wall mannoprotein. A SRB1/PSA1 null mutation is lethal whereas a decrease in SRB1/PSA1 function (by inhibiting the expression of SRB1/PSA1) leads to defects in bud growth, bud site selection, and cell separation, in addition to increases in cell permeability and cell lysis.

Another gene which regulates the cell wall is PDE2 (the gene encoding a high-affinity cAMP phosphodiesterase) which is part of the RAS/cAMP dependent pathway in yeast. We recently identified PDE2 as a multi-copy suppressor of srb1-1 (a mutation which depends on sorbitol for growth). Moreover, strains carrying a pde2 deletion share a number of phenotypes with srb1-1 mutants, including lysis upon osmotic shock.

The yeast cell wall influences the characteristics of the yeast cell in a number of ways and it is desirable to modulate the wall to confer desirable properties on yeast.

For instance, the yeast cell wall acts as a barrier which can obstruct the liberation of protein expressed within yeast cells. This effect is of particular significance to the biotechnology industry which uses yeasts for protein production and for the production of recombinant proteins in particular. For some proteins, it is possible to use the yeast secretion pathway to release the protein from the cell, thus obviating the need for mechanical or enzymic degradation of the cell wall. However, many proteins cannot be exported by the secretion pathway and are retained within the cell in a membrane-associated form. Some protein complexes, such as virus-like particles (VLPs) are also impossible to recover by the secretion route. It may be seen, therefore, that the rigid cell wall of yeast is a major barrier to the efficient operation of downstream processes leading to protein isolation and purification. In the food industry, yeast cell extracts are used as dietary supplements and flavourings, again requiring efficient methods of cell lysis that do not compromise the nutritional or organoleptic properties of the yeast cell extract.

The use of lysis mutants represent an alternative to mechanical/chemical disruption for the efficient recovery of yeast cell contents. Some attempts have been made to develop such mutants. For instance, WO 92/01798 concerns the use of a srb1-1 mutant. However this specification related to a DNA sequence deposited under the Budapest treaty which was first believed to code for the SRB1 gene but has since been shown to be the PDE2 gene. WO 96/02629 also relates to a lysis mutant and concerns the use of a mpk1/slt2 mutant which is stated to release intracellular proteins, including VLPs, following a temperature shift and osmotic shock. However, the application of both types of lytic mutants has significant drawbacks. The osmotic stabiliser required to enable the growth of a srb1-1 mutant is either expensive (sorbitol) or corrosive to the fermentor (NaCl) thus precluding the use of this mutant nil in large-scale processes. The temperature shift involved in the use of the mpk1/slt2 mutant requires considerable energy input and can also trigger the degradation or re-modelling of the proteins released from the lysed cells.

It is therefore an object of the present invention to provide yeast mutants which obviate or mitigate the above-mentioned disadvantages.

According to a first aspect of the invention, there is provided a yeast cell containing the SRB1/PSA1 gene and the PKC1 gene or functional derivatives thereof each operatively linked to a heterologous inducible promoter.

We have found that yeast cells containing the SRB1/PSA1 gene and the PKC1 gene or functional derivatives thereof each operatively linked to an inducible promoter (e.g. the cells according to the first aspect of the invention) may be used in applications where the induction of cell lysis is desirable. For instance, induction of yeast cell lysis is useful for isolating protein expressed within a yeast cell which is not readily secreted into the medium in which the cells are growing. Thus according to a second aspect of the present invention, there is provided a method of regulating yeast cell lysis comprising:

(i) growing yeast cells containing the SRB1/PSA1 gene and the PKC1 gene or functional derivatives thereof each operatively linked to an inducible promoter in a growth medium which activates the inducible promoter such that SRB1/PSA1 and PKC1 are expressed from said cells; and (ii) when lysis is required, growing the cells in a modified growth medium which represses SRB1/PSA1 and PKC1 expression such that cell lysis is induced.

The present invention is based upon our efforts to develop conditional lysis mutants that do not require special media in which to grow (e.g. sorbitol supplemented) or temperature shifts. We placed various genes that have been shown to contribute, in different ways, to cellular integrity of *S. cerevisiae* under the control of inducible promoters and examined A whether or not repression of the gene (by altering the composition of the media in which the yeast is grown such that the promoter is inactivated) modulates cell lysis. We found that repression of some of the genes tested, for instance PDE2, did not significantly influence lysis. These genes were therefore unsuitable candidates to be modulated to generate an improved lytic yeast strain.

We found that repression of the SRB1/PSA1 gene in yeast cells grown in normal media resulted in a reduction in cell growth, cells gradually losing their viability and integrity and the release of about 7% of total protein into the medium 24 hours after repression was induced. Furthermore we found that repression of PKC1 led to more extensive release of cellular protein into the medium (approximately 18% of total protein into the medium 24 hours after repression was induced) although cell growth was not significantly altered. These results were expected because, although it is known that yeast cells carrying the srb1-1 allele can grow in osmotically-buffered media, such mutanits lyse upon hypoosmotic shock. It is also known that cells bearing the pkc1 mutation can grow in osmotically-bufferred media (e.g. in the presence of 10% (w/v) sorbitol) but quickly lyse upon osmotic shock.

We also repressed expression of both SRB1/PSA1 and PKC1 in yeast cells and found that under these circumstances the yeast cultures underwent substantial lysis which permitted the efficient release of both homologous and heterologous proteins from the yeast. In fact, as illustrated in Example 1, lysis was surprisingly more extensive than observed for cells in which SRB1/PSA1 and PKC1 were repressed singularly (about 30% of total protein was released into the medium 24 hours after repression was induced) which shows that the lysis phenotype conferred by the repression of SRB1/PSA1 and PKC1 was additive. Thus cells according to the first aspect of the invention are of particular utility as it is possible to grow the cells without significant lysis and then at a predetermined time during the fermentation induce extensive lysis of the yeast cells.

Cells according to the first aspect of the invention may be formed from yeast strains with normal SRB1/PSA1 and PKC1 expression. Preferably the yeast is *Saccharomyces cerevisiae* or strains thereof. Examples of such yeast strains include ZO123 and FY23. The conservation of gene function in different yeast species means that other types of yeasts (particularly those that are currently exploited for heterologous gene expression such as *Pichia pastoris*, *Hansenula polymorpha* and *Kluyveromyces lactis*) may be used to form cells according to the first aspect of the invention in which their SRB1/PSA1 and PKC1 homologues are operatively linked to an inducible promoter.

The endogenous promoters of the SRB1/PSA1 gene and the PKC1 gene are not readily inducible in such strains and it is therefore necessary to modify genetically yeast such that SRB1/PSA1 and PKC1 expression from the yeasts is inducible. This may be achieved in a number of ways. For instance, yeast cells may be transformed with DNA molecule(s) comprising an inducible promoter(s) such that the inducible promoter(s) take over control of transcription of the endogenous SRB1/PSA1 and PKC1 genes. These DNA molecules are preferably designed such that they will integrate into the yeast genome and replace the region of DNA containing the endogenous SRB1/PSA1 and PKC1 promoters (as appropriate). As a result the inducible promoter introduced into the cell becomes operatively linked to the SRB1/PSA1 and PKC1 genes and can control their expression. Alternatively the cells may be transformed with a first recombinant DNA molecule comprising an inducible promoter operatively linked to the SRB1/PSA1 gene and/or a second recombinant DNA molecule comprising an inducible promoter operatively linked to the PKC1 gene. These recombinant DNA molecules are designed such that they will integrate and replace by homologous recombination the endogenous SRB1/PSA1 and PKC1 genes respectively. The DNA molecules and recombinant DNA molecules used for transforming yeast cells are preferably incorporated in a suitable vector which bears a DNA sequence which allows homologous recombination between the vector and the DNA at the site of the endogenous promoter/gene.

The cells according to the first aspect of the invention may also be derived from yeasts which are srb1-1 and/or pkc mutants. These mutants have a lytic phenotype and are only able to survive when grown in osmotically buffered media. However we have found that these cells may be transformed with an expression cassette comprising an inducible promoter and DNA sequences encoding suitable genes to replace the mutated gene to form cells according to the first aspect of the invention which display a normal phenotype (i.e. they are not osmotically sensitive or liable to lyse spontaneously) in permissive growth media conditions (which allows activation of the inducible promoter) but will lyse when the media is modified such that gene expression is repressed. Yeast cells to be modified may be transformed with the abovementioned recombinant DNA molecules (or vectors bearing such molecules) to form cells according to the first aspect of the invention in which the recombinant DNA molecules either integrate into the genome of the mutant yeast or which may subsist (and ideally autonomously replicate) in the cytosol of the yeast cell. Examples of srb1-1 and/or pkc mutant cells which may be used include the ZO124 strain of *Saccharomyces cerevisiae*.

The SRB1/PSA1 gene and the PKC1gene (or functional derivatives thereof) may each be operatively linked to a number of inducible promoters. The inducible promoter may, for example, be the GAL1 promoter (inducible by galactose) or the TET promoter (inducible by tetracyclin).

Preferred promoters are ones which may be regulated by an agent contained within the media within which the cells are grown. Such agents are ideally readily available, inexpensive, soluble in normal yeast growth medium and do not adversely effect proteins released from lysed cells. We have found that the methionine regulated promoter, pMET3 (Mountain et al., 1991 Yeast 7: 781–803) fulfils these criteria as its modulator (methionine) may be easily included or excluded in growth medium as required. Thus pMET3 is a preferred promoter.

The pMET3 promoter drives gene expression in the absence of methionine. Therefore in methionine-free media SRB1/PSA1 and PKC1 expression occurs. However when the media is modified by the addition of methionine, gene expression is repressed and cell lysis induced.

DNA sequences corresponding to pMET3 may be used as a DNA molecule for transforming yeast cells although it is preferred that pMET3 is contained within a vector (i.e. as part of a larger DNA molecule containing other functional elements). A preferred vector, named pRS316-pMET3, comprises a pRS316-based plasmid (described in Sikorski & Heiter (1989) Genetics 122: 19–27) which contains the MET3 promoter (Yeast cenome Accession no. X06413). The construction of pRS316-pMET3 is described in detail in Example 1.

pRS316-pMET3 may be used to form recombinant vectors which contain preferred recombinant DNA molecules pMET3-PKC1 and pMET3-SRB1.

Preferred derivatives of pRS316-pMET3 which contain pMET3-PKC1 include pRS316-pMET3-PKC1 is described in detail in Example 1. Other preferred derivatives of pRS316-pMET3 are designed to allow integration of the pMET3-PKC1 regulation cassette at the homologous PKC1 locus. For instance, pRS316-$F_1F_2$-pMET3-PKC1 is constructed by inserting a PKC1 upstream flanking region (which was designated $F_1F_2$ and has the nucleotide sequence listed below) between the KpnI and SphI sites of pRS316-pMET3-PKC1.

Nucleotide sequence of the $F_1F_2$ DNA fragment:
ACAAGCAGCTGATGAAAAGCCAAGACAT-AAGTATTGT TGCCCACACT GTGGGTCTTC-ATTTCCAAGATGTGCCATATGTCTCAT-GCCTCTAGGAA CGTCAAACTTACCTTTTG-TAATAAATGGGACGCAATCACGCGATCAAT GCAGACAGAAGACTCTCAAGATGGTG-CAAATCGCGAACTCGTAAGTA GAAAACT-GAAGTTGAACGAGTGGTTCAGCTTCCT-GTTTGAGTTGCAACCA TGGTATGCA-TGCCGGTCACGCTGAAGAATGGTTTGA-CAGACATAATGTT TGTCCACTCCAGGTT (SEQ. I.D. NO.14)

pRS316-$F_1F_2$-pMET3-PKC1 may also be further modified to introduce the TRP1 gene as a selectable marker (a DNA molecule corresponding to Yeast genome accession No. V01341 or J01374) between the SphI and SalI sites to form the construct pRS316-$F_1$F2-TRP1-pMET3-PKC1. pRS316-$F_1F_2$-TRP1-pMET3-PKC1 is particularly useful when forming cells according to the first aspect of the invention because it may be digested with KpnI and SacI and the fragment containing $F_1F_2$-TRP1-pMET3-PKC1 used to transform a host yeast strain.

SRB1.9e is a preferred recombinant vector which contains the recombinant DNA molecule pMET3SRB1 and is described in more detail in Example 1. Plasmid pSRB1-9e is particularly useful when forming cells according to the first aspect of the invention because it may be digested with ApaI and BstI107I and the pMET3-SRB1-LEU2 fragment obtained in this way used to transform a yeast cell.

Preferred cells according to the first aspect of the invention may be formed using the above described constructs. For instance, yeast strain ZO-123 (MATa his3 leu2 trp1 ura3) which expresses both SRB1/PSA1 and PKC1 may be modified such that the transcription of the endogenous SRB1/PSA1 and PKC1 genes are brought under the control of pMET3 (e.g. by integrating pMEFT3 into the yeast genome such that it replaces the endogenous SRB1 and PKC1 promoters). Alternatively pRS316-$F_1$ $F_2$-pMET3-PKC1 or pRS316-$F_1F_2$-TRP1-pMET3-PKC1 in conjunction with SRB1.9e may be used to integrate the pMET3-PKC1 and pMET3-SRB1 cassettes respectively into ZO-123 to form ZO-127 which is a particularly preferred cell according to the first aspect of the invention.

We have found that lysis may be regulated according to the method of the second aspect of the invention by growing yeast cells according to the first aspect of the invention in a growth medium which activates the inducible promoter such that SRB1/PSA1 and PKC1 are expressed from said cells. Then, after a predetermined time, the cells may be switched to growth in the modified growth medium such that SRB1/PSA1 and PKC1 expression is repressed and cell lysis induced.

The manner in which SRB1/PSA1 and PKC1 gene expression is regulated according to the method of the second aspect of the invention will depend upon which inducible promoter is being used. This regulation is dependent upon the exact concentration of an agent capable of modulating promoter activity contained within the growth medium. We have found that addition to the media of methionine to a concentration of between 0.05 mM and 20 mM will inhibit expression of SRB1/PSA1 and PKC1 from cells transformed with pMET3-SRB1 and pMET3-PKC and thereby induce lysis whereas the same cells grown in the absence (or minimal concentration) of methionine are able to grow unimpeded. Preferably a concentration of between about 0.05 mM and 5 mM methionine in the media and most preferably a concentration of about 2 mM methionine in the media is used to induce lysis.

The growth medium used according to the method of the second aspect of the invention should be readily adaptable such that it may be in either of two forms: one which permits activation of the inducible promoter and thereby SRB1/PSA1 and PKC1 expression; and a second form which is modified such that SRB1/PSA1 and PKC1 gene expression is repressed. This repression may be effected by removal of an agent which activates the promoter but is preferably effected by addition to the media of an agent which inhibits the promoter.

The growth medium should contain sufficient amounts of nutrients (i.e carbohydrate, nitrogen source etc) required to allow optimal, growth of yeast when SRB1/PSA1 and PKC1 are not being repressed.

The exact composition of the medium depends upon a number of factors (for instance the specific yeast used). Purely by way of example a suitable growth medium is F1 medium which comprises:

Mineral Salts Final Concentration in F1-Medium

| Ammonium sulphate | 3.13 g/l |
| Potassium dihydrogen orthophosphate | 2.00 g/l |
| Magnesium sulphate 7-hydrate | 0.55 g/l |
| Sodium chloride | 0.10 g/l |
| Calcium chloride dihydrate | 0.09 g/l |

Trace Elements

| Zinc sulphate 7-hydrate | 0.07 mg/l |
| Ferric chloride 6-hydrate | 0.05 mg/l |
| Cupric sulphate | 0.01 mg/l |
| Boric acid | 0.01 mg/l |
| Potassium iodide | 0.01 mg/l |

Vitamins

| Inositol | 62.00 mg/l |
| Thiamine Hydrochloride | 14.00 mg/l |
| Pyridoxine | 4.00 mg/l |
| Calcium Pantothenate | 4.00 mg/l |
| d-Biotin | 0.30 mg/l |

+ carbohydrate substrate
+/− agent which modulates the inducible promoter

The composition of the media and the modified form thereof ideally only differ by the inclusion or exclusion of an agent which modulates the inducible promoter. The type of agent used will depend upon which specific promoter is used. When cells are used in which SRB1/PSA1 and PKC1 are operatively linked to the pMET promoter, the media permissive for yeast cell growth should be free of methionine. Methionine may be added to the medium as required to form the modified media in which lysis is induced.

The method of the second aspect of the invention may be readily adapted for the purposes of isolating protein from yeast cells. Once yeast cells have been lysed yeast cell debris/hosts may easily be separated from the protein released from the cells (e.g. by filtration, sedimentation and/or centrifugation). The protein may then be further purified using conventional biochemical techniques. The method is most suitable for isolating recombinant proteins expressed from genetically engineered yeast cells.

Another characteristic of yeast which is determined by the cell wall is its ability to flocculate. Unlike adhesion in mating, which is induced by highly specific pheromones, flocculation is an asexual aggregation of cells which is a very useful characteristic in industrial yeast strains. Flocculation is exploited in fermentations such as beer-brewing, wine-making, and fuel ethanol production because it leads to efficient separation of cells from the fermentation liquor.

Two types of flocculation phenotypes have been described. The FLO1 type, caused by FLO1/FLO5/FLO8, is $Ca^{2+}$-dependent and inhibited by mannopyranoses. The NewFlo phenotype, on the other hand, is prevented by both manno- and glucopyranoses. The FLO1 gene, which is located on chromosome 1, has been reported to encode a GPI-anchored, cell surface protein with its amino terminus exposed to the medium. FLO5 is highly homologous to FLO1 and is also found on chromosome 1. FLO8, previously mapped to chromosome 1 and said to be allelic to FLO1 has recently been reassigned to chromosome V and demonstrated to mediate flocculation via transcriptional activation of FLO1. More recently, a new flocculation gene, named FLO2, has been cloned and localised to chromosome XII; its function remains unclear, although it can complement flo1 mutations. Other genes, like TUP1 and SNN6, also act on yeast cell flocculation via transcriptional regulation.

Flocculation in *S. cerevisiae* is thought to be a result of interactions between lectin-like cell surface proteins (termed flocculins), encoded by the FLO genes. and the cell wall mannan. This hypothesis is supported by the following findings: loss of flocculation capacity following protease treatment, efficient dispersion of flocs by mannose and its derivatives and the failure of certain mnn mutant cells to co-flocculate with flocculant cells. So far, studies of flocculation have centred on the cloning and characterisation of dominant flocculation genes and the elucidation of their transcriptional regulation. Less attention has been paid to the effect of changes of cell wall structure on flocculation.

We have found that cells in which the PKC1 and/or SRB1/PSA1 gene or functional derivatives thereof are operatively linked to heterologous promoters may be used in applications in which the induction of flocculation is desirable (e.g. fermentation reactions such as for the production of alcohol).

According to a third aspect of the present invention, there is provided a method of regulating yeast cell flocculation comprising:

(i) growing yeast cells containing the PKC1 gene or functional derivatives thereof operatively linked to an inducible promoter in a growth medium which activates the inducible promoter such that PKC1 is expressed; and (ii) when flocculation is required, growing the cells in a modified growth medium which represses PKC1 expression such that flocculation is induced.

According to the third aspect of the invention we have found that the repression of PKC1 expression makes it possible to induce flocculation. Therefore cells containing the PKC1 gene or functional derivatives thereof operatively linked to a heterologous inducible promoter (such as pMET3) are useful when it is desired to induce flocculation. Such cells are particularly useful when the simultaneous induction of lysis and flocculation is required (as PKC1 repression also causes lysis). The induction of lysis and flocculation is desirable when purifying proteins released from yeasts. The induced lysis liberates the contents of the cell whereas the induced flocculation will favour sedimentation of the cell ghosts/debris and thereby separate cell contents (which will remain in the media) from the cell ghosts/debris.

Cells suitable for use according to the method of the third aspect of the invention include cells in which only PKC1 is under the regulation of an inducible promoter and include:

(i) ZO124 transformed with pRS316-pMET3-PKC1, pRS316-$F_1F_2$-pMET3-PKC1 or pRS316-$F_1F_2$-TRP1-pMET3-PKC1 (see Example 1);

(ii) ZO123 transformed with pRS316-pMET3-PKC1 or pMET3-PKC1 containing fragments derived from pRS316-$F_1F_2$-pMET3-PKC1 or pRS316-$F_1F_2$-TRP1-pMET3-PKC1 (see Example 1); and (iii) yeast strain ZO-126 (see Example 2).

We have also found that cells may be developed which have a flocculating phenotype by removing SRB1/PSA1 from under the control of its endogenous promoter and placing the gene under the control of a heterologous promoter (which may be inducible or constitutive). Such cells flocculate but do not lyse to a significant extent and are therefore useful in industrial applications where flocculation is of primary importance (e.g. for sedimenting yeast during the brewing process). Thus according to a fourth aspect of the invention there is provided a method of fermentation comprising growing yeast cells containing the SRB1/PSA1 gene or functional derivatives thereof operatively linked to a heterologous promoter in a growth medium in which SRB1/PSA1 expression is regulated by the heterologous promoter whereby said cells flocculate.

SRB1/PSA1 expression may be regulated in cells used according to the fourth aspect of the invention by an inducible promoter or a constitutive promoter. pMET3 is a preferred promoter for regulating SRB1/PSA1 expression in cells used according to the fourth aspect of the invention.

Examples of cells in which SRB1/PSA1 is under the regulation of an inducible promoter include:

(i) ZO125 (ZO 123 cells transformed with pMET3-SRB1); and (ii) FY23SRB1$^{MET3}$.

Although we do not wish to be bound by any hypothesis we believe that the flocculation phenotype caused when SRB1/PSA1 is transcribed from pMET3 is not due to the gene's underexpression but, rather, is the result of its constitutive expression. Cell viability is not affected by the constitutive expression of SRB1/PSA1, suggesting that sufficient Srb1/Psa1p is synthesised under the control of pMET3 to allow yeast to go through its cell cycle. However, when SRB1/PSA1 is expressed from its own promoter, its transcription level increases some 4- to 6-fold at START. Thus the constitutive expression of SRB1/PSA1 from pMET3 could hyperactivate glycosylation at all other cell cycle phase which may lead to enhanced cell growth and flocculation.

According to a fifth aspect of the invention there is provided a method of fermentation comprising growing yeast cells containing the SRB1/PSA1 and PKC1 gene or functional derivatives thereof operatively linked to a heterologous promoter in a growth medium in which SRB1/PSA1 and PKC1 expression is regulated by the heterologous promoter whereby said cells flocculate.

We believe cells used according to the method of the fifth aspect of the invention have a flocculating phenotype because SRB1/PSA1 is not regulated by its endogenous promoter in such cells. These cells may comprise:

(i) PKC1 operatively linked to an inducible promoter and SRB1/PSA1 linked to any heterologous promoter; or (ii) both PKC1 and SRB1/PSA1 operatively linked to an inducible promoter (i.e. cells according to the first aspect of the invention).

The method of the fifth aspect of the invention may be used when it is desirable to induce lysis (e.g. according to the method of the second aspect of the invention) at a predetermined time during the fermentation as well as flocculation. For instance, this may be achieved by adding methionine (0.05 mM–20 mM) to the growth medium when PKC1 is operatively linked to a methionine regulated promoter such as pMET3.

According to a sixth aspect of the invention, there is provided a yeast cell containing the PKC1 gene or functional derivatives thereof operatively linked to a heterologous inducible promoter.

Cells according to the sixth aspect of the invention may be employed in the method according to the third aspect of the invention. Such cells may contain the PKC1 gene or functional derivatives thereof operatively linked to any inducible promoter described above for use in cells according to the first aspect of the invention.

Preferred cells according to the sixth aspect of the invention include:

(i) ZO124 transformed with pRS316-pMET3-PKC1, pRS316F$_1$F$_2$-pMET3-PKC1 or pRS316-F$_1$F$_2$-TRP1-pMET3-PKC1 (see Example l);

(ii) ZO123 transformed with pRS316-pMET3-PKC1 or pMET3-PKC1 containing fragments derived from pRS316-F$_1$F$_2$-pMET3-PKC1 or pRS316-F$_1$F$_2$-TRP1-pMET3-PKC1 (see Example 1); and (iii) yeast strain ZO-126 (see Example 2).

According to a seventh aspect of the invention, there is provided a yeast cell containing the SRB1/PSA1 gene or functional derivatives thereof operatively linked to a heterologous promoter.

Cells according to the seventh aspect of the invention may be employed in the method according to the fourth aspect of the invention. Such cells may contain the SRB1/PSA1 gene or A functional derivatives thereof operatively linked to any heterologous promoter (including inducible promoters). Preferred promoters are described above for use in cells according to the first aspect of the invention.

Examples of cells according to the seventh aspect of the invention include:

(i) ZO125 (ZO 123 cells transformed with pMET3-SRB1); and (ii) FY23SRB1$^{MET3}$.

According to a eighth aspect of the invention, there is provided a yeast cell containing the PKC1 gene or a functional derivative thereof operatively linked to a heterologous inducible promoter and the SRB1/PSA1 gene or a functional derivative thereof operatively linked to a heterologous promoter.

Cells according to the eighth aspect of the invention may be employed according to the method of the fifth aspect of the invention. Such cells may be the same as cells according to the first aspect of the invention except the SRB1/PSA1 gene or a functional derivative thereof may be operatively linked to any heterologous promoter.

Optimal growth of yeasts used according to either the methods of the second or third aspects of the invention can be dependent upon the fermenter in which the yeast are grown. Fermenters will usually comprise one or more of:

1. Rotors or similar devices for agitating the yeast culture.
2. An air (or oxygen) supply.
3. An inlet for addition of nutrients or agents which modify the medium.
4. A means of extracting waste products and/or proteins produced
5. A thermostat and means of regulating temperature.

Preferred fermenters are those already known to the art for the culture of yeast. The type of fermenter used will depend upon whether the yeast cells are being grown in the laboratory by potage, as a pilot plant or in full industrial scale-up (e.g. for industrial production of yeast proteins).

When cells are cultured in the modified growth medium (which represses SRB1/PSA1 and PKC1 expression such that lysis is induced) according to the second aspect of the invention, the culture conditions do not need be as stringently regulated as during the growth phase because cell viability is not relevant when lysis is induced. However it will be appreciated that the media should not be allowed to change (e.g. undesirable pH or temperature changes) such that the liberated yeast cell contents (e.g. a recombinant protein) are denatured or corrupted.

The culture conditions required for cells grown in modified growth medium according to the third aspect of the invention will depend upon whether flocculation only (whilst maintaining cell viability) or whether flocculation and lysis is desired. If it is desired to maintain viability similar culture conditions as used for growth in the permissive media should be maintained whereas if lysis is to be induced the comments of the preceding paragraph apply.

The present invention will now be described, by way of example, with reference to the accompanying drawings in which FIG. 1 schematically represents the DNA sequences inserted into the pRS316 vector in the construction of pRS316-pMET3 (a), pRS316-pMET3-PKC1 (b) and pRS316-F$_1$F$_2$pMET3-PKC1 (b);

FIG. 2. is a graph illustrating the effect of SRB1 repression on cell viability and cell lysis in Example 1;

FIG. 3. is a graph illustrating the effect of PKC1 repression on cell viability and cell lysis in Example 1;

FIG. 4. is a graph illustrating the effect of dual SRB1 and PKC1 repression on cell viability and cell lysis in Example 1;

FIG. 5. is a bar chart illustrating the GFP released from SRB1 and PKC1 repressed cells (ZO127/Pope-2$\mu$) in Example 1;

EXAMPLE 1

Figure 1:
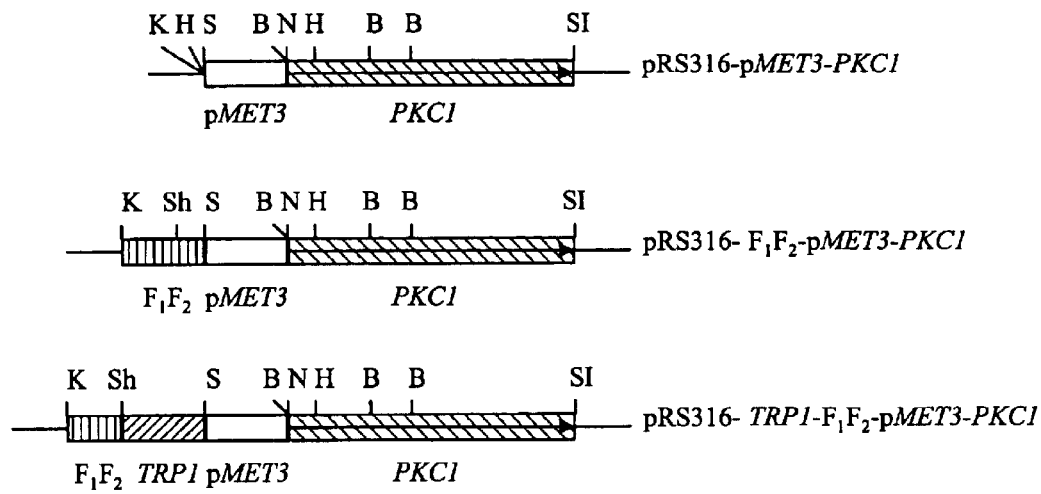

Yeast according to the first aspect of the invention were made by transforming suitable yeast strains and the extent of inducible cell lysis assessed relative to single SRB1 and PKC1 mutants.

1.1 Materials and Methods
1.1.1 Stains

Strains of *Saccharomyces cerevisiae* used in this study are listed in Table 1 together with relevant references and sources.

TABLE 1

*S. cerevisiae* strains used in this study

| Yeast strains | Relevant phenotype |
|---|---|
| FY23 | MATa ura3-52 leu2-Δ1 trp1-Δ63 |
| FY23-SRB1$^{MET3}$ | MATa ura3-52 leu2-Δ1 trp1-Δ1 psa1Δ::pMET3- SRB1-LEU2 |
| ZO123 | MATa his3 leu2 trp1 ura3 |
| ZO124 | MATa his3 leu2 trp1 ura3 pkc1::LEU2 |
| ZO125 | MATa his3 leu2 trp1 ura3 psa1Δ::pMET3-SRB1-LEU2 |
| ZO126 | MATa his3 leu2 trp1 ura3 pkc1Δ::TRP1-pMET3-PKC1 |
| ZO127 | MATa his3 leu2 trp1 ura3 pkc1Δ::TRP1-pMET3-PKC1 psa1Δ::pMET3- SRB1-LEU2 |

Bacterial strains (JM109 and XL1-Blue, Premega) were grown in LB and LB+ ampicillin, prepared as described by Sambrook et al. (Molecular Cloning: a laboratory manual. 2nd ed. Cold Spring Harbor Laboratory Press, Cold Spring Harbor, N.Y., 1989).

1.1.2 Media

Yeast growth media (YEPD, minimal,) were prepared as described by Sherman et al. (Methods in yeast genetics. Cold Spring Harbor Laboratory press, Cold Spring Harbor, N.Y., 1986) and Kaiser et al. (Methods in Yeast Genetics. Cold Spring Harbor Laboratory Press, Cold Spring Harbor, N.Y., 1994). All media used for the lysis test were supplemented with 10% w/v sorbitol.

Selective drop-out media (modified growth medium) with appropriate combinations of bases and amino acids (e.g. +/−methionine)

1.1.3 Oligonucleolides and PCR

The sequences of the oligonucleotides employed in this study, and their utility, are given in Table 2. All PCR reactions were performed using pwo DNA polymerase (Boehringer Mannheim) according to the recommendation of the manufacturer. PCR fu products were purified (using a Qiagen kit, cat no. 28036) to eliminate primer dimers, salts, oligonucleotides and enzymes prior to restriction digestion.

1.1.4 Plasmids, DNA Preparation and Manipulations.

The plasmids employed in this study are listed in Table 3. Bacterial plasmid DNA was isolated using the alkaline-lysis method of Bimboim and Doly (*Nucl. Acids Res.* 7: 1513–1523, 1979) as described by Sambrook et al. (supra). All DNA fragments used for sub-cloning were either PCR amplified and purified using a Qiagen kit (Cat. no. 28036) or gel-purified by the method of Heery et al. (*Trends Genet.* 6: 173, 1990) after appropriate restriction enzyme digests. Enzymatic reactions with restriction enzymes, T4 DNA ligase, calf intestinal phosphatase and T4 DNA polymerase, were performed according to the recommendations of the manufacturers. Yeast genomic DNA was isolated from 5 ml of yeast culture according to the method of Kaiser et al. (Methods in Yeast Genetics. Cold Spring Harbor Laboratory Press, Cold Spring Harbor. N.Y., 1991)

TABLE 2

Oligonucleotides used in the study

| SEQ ID No | Sequence | Description | Incorporation Site |
|---|---|---|---|
| 1 | GAAA GCGGCCGC AAA AGT AAG TAT AGT ATC AC (SEQ ID NO:1) | PKC1 forward primer | NotI |
| 2 | CCT GAGCTC CAA GAT AGG TAC GAA CAA AA (SEQ ID NO:2) | PKC1 reverse primer | SacI |
| 3 | CCG GGT ACC ACA AGC AGC TGA TGA AAA GCC A (SEQ ID NO:3) | PKC1 flanking region ($F_1F_2$) forward primer | KpnI |
| 4 | ACGC GTC GAC AAC CTG GAG TGG GAC AAA CAT (SEQ ID NO:4) | PKC1 flanking region ($F_1F_2$) reverse primer | SalI |
| 5 | CAT GCATGC TAA TAT AGG AAG CAT TTA ATA (SEQ ID NO:5) | TRP1 forward primer | SphI |
| 6 | ACGC GTCGAC GCA AGT GCA CAA ACA ATA CTT (SEQ ID NO:6) | TRP1 reverse primer | SalI |
| 7 | ATT ATT CTC CAT GCG AGC CAGG (SEQ ID NO:7) | $F_1F_2$-TRP1-pMET3-PKC1 integration check primer | |
| 8 | CAT GCT GCC TAT GTT GCA (SEQ ID NO:8) | pMET3-SRB1-LEU2 integration check primer | |
| 9 | ACG ACA GAG AGA GAC CCA AG (SEQ ID NO:9) | pMET3 reverse primer | |
| 10 | TGT CGA TTG GTG GGC ATT TGGG (SEQ ID NO:10) | PKC1 diagnostic primer 1 | |
| 11 | CGT CAT GAA CTC TCG CGG ATT TGA TA (SEQ ID NO:11) | PKC1 diagnostic primer 2 | |
| 12 | CGC GGA TCC AGC CAC AAG ACA AGC TAC AAC (SEQ ID NO:12) | SRB1 forward primer | BamH1 |
| 13 | ACT AGC ATG CAA TAC TAC AGA CAT TGA TAG CCA A (SEQ ID NO:13) | SRB1 reverse primer | Sph1 |

TABLE 3

Plasmids

| Plasmid | Description | Ref |
|---|---|---|
| pHAM8 | pUC19 derivative containing MET3 gene | Mountain et al., 1991 Yeast 7: 781–803 |
| pRS314 | pBLUESCRIPT-based *S.cerevisiae*/*E.coli* shuttle vector containing TRP1 and an ARS4-CEN6 fragment | Sikorski & Heiter (1989) Genetics 122: 19–27 |

TABLE 3-continued

Plasmids

| Plasmid | Description | Ref |
|---|---|---|
| pRS316 | pBLUESCRIPT-based S.cerevisiae/E.coli shuttle vector containing URA3 and an ARS4-CEN6 fragment | Sikorski & Heiter (1989) Genetics 122: 19–27 |
| YEplac195-PKC1 | YEplac195 derivative containing a 4.5 kb PKC1 fragment at the unique SphI site | Accession No. X75459 or L26355 |
| SRB1.9e | SRB1.9d derivative containing pMET3-PSA1 cassette instead of PSA1 and its homologous promoter | see Example 1 |
| pRS316-pMET3 | pRS316 derivative containing MET3 promoter | see Example 1 |
| pRS316-pMET3-PKC1 | pRS316 derivative containing MET3 promoter and PKC1 coding sequence | see Example 1 |
| pRS316-$F_1F_2$-pMET3-PKC1 | pRS316 derivative containing PKC1 upstream region, MET3 promoter and PKC1 | see Example 1 |
| pRS316-$F_1F_2$-TRP1-pMET3-PKC1 | pRS316 derivative containing PKC1 upstream region, TRP1, MET3 promoter and PKC1 | see Example 1 |
| Pope-$2\mu$ | pFAKanMx4-based vector containing a $2\mu$ replicator and GFP under the control of RAD54 promoter | Walmsley et al. (1997) Yeast 13: 15–35 |
| pUC19 | E. coli vector (Accession No M77789) | Yamish-Perron et al. (1985) Gene 33: 103–119 |
| YCp50 | CEN-ARS-URA3 shuttle vector | Rose et al. (1987) Gene 60: 237–243 |
| YEp13 | $2\mu$ LEU2 shuttle vector | Broach et al. (1979) Gene 8: 121–133 |
| YEplac195 | | Accession No. X75459 or J01374 |
| pSRB1-2 | 14.5 kb chromosome IV fragment in YCp50 | Gardner at al. (1996) Yeast 12: 411–413 |
| pSRB1-9b | claI-BamH1 fragment of pSRB1-2 in pRS316 | see Example 1 |
| pSRB1-9d | pSRB1-9b with LEU2 in NsiI-NheI sites | see Example 1 |

1.1.5 Transformation.

*Escherichia coli* strains were transformed by electroporation with a Gene Pulser Apparatus as recommended by the manufacturer (Bio-Rad). Yeast strains were transformed either by a modification of the lithium procedure of Ito et al. (*J. Bacteriol.* 153: 163–168, 1983), developed by Philipova (1985 Ph.D. Thesis, Institute of Molecular Biology, Bulgarian Academy of Science, Sofia, Bulgaria) and described by Stateva et al. (*Mol. Cell. Biol.* 11: 4235–4243, 1991), or according to that of Hill et al. (*Yeast* 2: 163–167, 1991).

1.1.6 Lysis Test and Viability Test

Osmotic lysis tests were performed as described by Stateva et al. (supra) except that viability assays were not carried out in this study. Lysis data were normalised as the number of A260 units released per A600 unit of pre-lysis cell suspension.

For the viability tests, cells were counted using a haemacytometer, diluted, and then plated onto appropriately supplemented solid media. Viability is represented as the number of cells which grow on plates (multiplied by any dilution factor), calculated as percentage of the total number of counted cells.

1.1.7 Methionine Regulation of the pMET3 Expression Cassettes

Cultures of strains containing pMET3-regulated cassettes were grown in permissive growth medium until early exponential phase (OD600 nm=0.05), at which point they were split into two halves. To one half of each culture, methionine was added to a final concentration of 2 mM (to form the modified growth media); to the other half, an equivalent volume of distilled water was added (controls). Cells were grown for additional periods of time for different purposes.

CONSTRUCTION OF RECOMBINANT DNA MOLECULES

1.1.8 Construction of pRS316-pMET3 pRS316-pMET3 is a pRS316-based plasmid which contains the MET3 promoter. The plasmid pHAM8 (Mountain et al., 1991 Yeast 7: 781–803) was used as a source of the MET3 promoter. It was digested with HindIII and EcoRV to release the pMET3-containing fragment (corresponding to the BgIII-EcoRV fragment of Yeast genome Accession No. X064113) which, after gel purification, was cloned into pRS316 (Sikorski & Heiter (1989) Genetics 122:19–27) that had been restricted with HindIII and SmaI. The resultant plasmid was named pRS316-pMET3.

1.1.9 Construction of pRS316pMET3-PKC1

DNA coding for PKC1 (Yeast genome accession number M32491) was obtained from a PCR using oligos 1 and 2 (Table 2) as primers and YEp195lac:PKC1 (Yep195lac of Accession No. X75459 or L26355 containing PKC1 DNA of Accession No. M32491) of as the template. The DNA was restricted with NotI and SacI, purified and cloned into pRS316-pMET3 between the NotI and SacI sites. The resultant plasmid was named pRS316-pMET3-PKC1.

1.1.10 Transformation of ZO124 with pRS316-pMET3-PKC1 pRS316pMET3-PKC1, was transformed into a pkc1::LEU2 yeast strain (ZO124, Table 1).

1.1.11 Construction of pRS316-$F_1F_2$-pMET3-PKC1 and pRS316$F_1F_2$-TRP1-pMET3-PKC1

To integrate the pMET3-PKC1 regulation cassette at the homologous PKC1 locus, a series of plasmids was constructed based on pRS316-pMET3-PKC1 (FIG. 1). First, the PKC1 upstream flanking region (which we designate $F_1F_2$) was inserted between the KpnI and SphI sites. $F_1F_2$ has the following DNA sequence:

ACAAGCAGCTGATGAAAAGCCAAGACAT-
AAGTATTGTTGCCCACACT GTGGGTCTT-
CATTTCCAAGATGTGCCATATGTCTCAT-
GCCTCTAGGAACGTCAAACTTACCTT- TTG-
TAATAAATGGGACGCAATCACGCGAT-
CAATGCAGACAGAAGACTCTCAAGATG-
GTGCAAATCGCGAACTCGTAAGTA GAAA-
ACTGAAGTTGAACGAGTGGTTCAGCT-
TCTGTTTGAGTTGCAACCA TGGTATGCATGC-
CGGTCACGCTGAAGAATGGTTTGACAGA-
CATAATGTT TGTCCCACTCCAGGTT (SEQ I.D. NO. 14)

Second, a TRP1 marker (a DNA molecule corresponding to Yeast genome accession No. V01341 or J01374) was cloned into pRS316-$F_1F_2$-pMET3-PKC1 between the SphI and SalI sites. Finally, the construct pRS316-$F_1F_2$-TRP1-pMET3-PKC1 was digested with KpnI and SacI and the fragment containing $F_1F_2$-TRP1-pMET3-PKC1 was used to transform a pkc1::LEU2 (ZO124, Table 1) host yeast strain. Transformants, which could grow up on medium without sorbitol and could not grow without leucine, were checked for correct integration by diagnostic PCR using two primer oligonucleotides (Oligos 5 and 6 in Table 2), one annealing to the TRP1 marker and the other to sequence just outside the F$_1$F$_2$ fragment. This should yield a 1.4 kb fragment and this was the case with transformant ZO 126 (data not shown).

1.1.12 Construction of pSRB1.9e pSRB1.9e was formed by making the following genetic manipulations of known DNA molecules/vectors:

(a) A ClaI-BamHI fragment from pSRB1-2 (a Yep50 recombinant plasmid comprising the SRB1/PSA1 gene—Gardner et al. (1996) Yeast 12:411–413) was ligated into pRS316 Sikorski & Helter supra) and the resulting construct named PSRB1.9b.

(b) The LEU2 gene on a SpeI-NsiI fragment isolated from Yep13 (described in Broach et al., 1979) was then cloned into pSRB1.9b to form pSRB1.9d.

(c) The SRB1/PSA1 coding sequence (without its promoter region) from pSRB1.9d was amplified in a PCR using the oligonucleotides of SEQ ID Nos. 12 and 13 as forward and reverse primers respectively (see Table 2). The PCR product was treated with BamHI and SphI and subcloned into Yep50 (described in Rose et al., 1987) digested with the same enzymes to produce the plasmid YCp50-SRB1.

(d) A HindIII-BamHI fragment (comprising the SRB1 gene) from YCp50-SRB1 was then ligated with pMET3 on a HindIll-BamHI fragment isolated from pRS316-pMET3 (see 1.1.8). The resultant construct was named YCp50-pMET3-SRB1.

(e) Finally, to allow integration into the SRB1/PSA1 locus in yeast strains such as FY23, pSRB1-9e was made. Plasmid pSRB1-9d was digested with HindIII and NsiI and ligated with the fragment comprising pMET3-SRB1 derived from digestion of YCp50-pMET3-SRB1 with the same restriction enzymes. The resultant plasmid pSRB1-9e may then be digested with ApaI and BstI 107I and the PMET3-SRB1-LEU2 fragment obtained in this way used to transform FY23.

1.1.13 Integration of pMET3-SRB1 in FY23

Integration of pMET3-SRB1 into yeast chromosome IV was achieved by transforming, into *S.cerevisiae* strain FY23, with the ApaI/BstI107I fragment of SRB1.9e containing SRB1/PSA1 upstream and downstream flanking regions, surrounding the pMET3- SRB1-LEU2. The strain was named FY23-SRB1 $^{MET3}$.

Transformants were selected by their inability to grow in the presence of 2 mM methionine and were checked for correct integration using suitable diagnostic primers. The diagnostic PCR should result in a 1.1 kb band (as was the case for FY23-SRB1 $^{MET3}$.

1.1.14 Construction of strain ZO127, Carrying Both pMET3-SRB1 and pMET3-PKC1 Integrated at their Respective Homologous Loci Plasmid SRB1.9e was digested with ApaI and BstI107I and the fragment containing SRB1/PSA1 upstream and downstream flanking regions, surrounding the pMET3SRB1-LEU2 cassette, was transformed into strain ZO126. Transformants which did not grow on medium containing 2 mM methionine and 10% (w/v) sorbitol were further checked for correct integration at the SRB1/PSA1 locus by diagnostic PCR as for FY23SRB1$^{MET3}$ (see Table 1). The resultant strain was named ZO127.

1.1.15 Measurement of Total Protein Release from Cells

Cells from 1–5 ml of culture grown at 30° C. and 250 rpm were washed and resuspended in 0.3ml breakage buffer (20 mM Tris-Cl, 1 mM EDTA, pH 7.5, 0.1 M NaCl) containing protease inhibitor (Boehringer-Mannheim, cat. no. 1 836 153). The suspension was transferred to a 1.5 ml microcentrifuge tube, to which 1 ml of 100 mg/ml zymolyase (ICN) was added. After incubation for 30 min. at 37° C., 0.3 g of 0.45–0.6 mm diameter glass beads (Sigma) were added. Cells were broken by vortexing four times at 4° C. for 1 min., with an intervening period of 1 min. on ice between treatments. The cell debris and buffer were then pipetted into a fresh tube. The beads were washed with a further 0.2 ml of breakage buffer and the supernatants combined. The solution was cleared by centrifugation at 12.000 g for 10 min. for total protein measurement.

The Bio-Rad protein assay was used since it is compatible with the amino acids contained in the minimal medium used. Protein samples were diluted to between 200$\mu$g and 1400 $\mu$l/ml. When samples contained less than 25$\mu$g/ml of protein, the micro-assay was performed. Total protein was calculated by combining cell extract protein with the protein released into the medium. The protein released into the medium was then expressed as a percentage of the total protein.

1.1.16 Measurement of Fluorescence and GFP Release from Cells

The plasmid Pope-2$\mu$ (Walmsley et al., 1997 Yeast 13:1535–1545) containing jellyfish GFP under the control of the RAD54 promoter was used to transform ZO127. 0.05% v/v methanesulfonic acid methyl ester (MMS, Sigma) was added to induce the expression GFP at very early exponential phase. For all GFP measurements, cells were grown at 25° C. and 250 rpm to avoid GFP misfolding. Cell extracts were isolated as above except that treatment with Zymolyase was carried out at 25° C. for 90 min. Fluorescence of the cell extract and lysate was determined using a 10 nm excitation window at 488 nm and a 5 nm emission window at 511 nm in a Perkin-Elmer luminescence spectrometer.

Since yeast proteins have a certain degree of fluorescence which means that it is impossible to differentiate homologous yeast proteins from GFP, ZO127 without GFP construct, grown under the same conditions, was included as the control. Brightness units for the control were defined as fluorescence divided by total protein in the cell extract and lysate (MII.3.2). We assumed that GFP constituted a negligible percentage of the protein in the cell extract or lysate of ZO127/Pope-2$\mu$ cells. So, fluorescence contributed by GFP in the cell extract of the sample was calculated as:

$$Fc-Prot.c \cdot Bc$$

where Fc stands for fluorescence in sample cell extract; Prot.c denotes total protein in sample cell extract; Bc is the brightness units of the control cell extract.

The fluorescence contributed by GFP released into medium was calculated in a similar way as:

$$Fm-Prot.m \cdot Bm$$

where Fm stands for fluorescence in sample medium (lysate); Prot.m denotes total protein in sample medium; Bm is the brightness units of the control medium. The yield of GFP released into the medium was obtained by dividing GFP in the medium by total GFP (GFP in the cell extract plus GFP in the medium).

Figure 2:
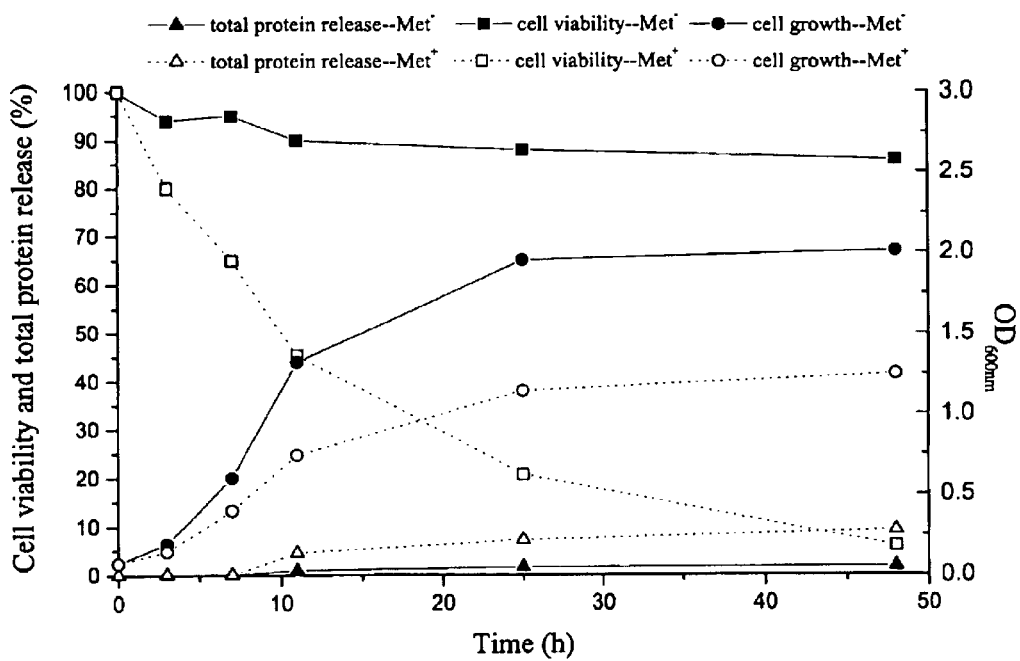

1.2 Results 1.2.1 Repression of SRB1 Leads to Gradual Cell Lysis and Release of Cellular Protein The use of the regulation cassette pMET3-SRB1 to determine the terminal phenotype of this essential gene has been studied by integrating the cassette at the SRB1/PSA1 chromosomal locus in a standard laboratory strain, FY23. The expression of SRB1/PSA1 was regulated by growing cells in minimal medium without methionine until the early exponential phase, at which point methionine was added. Cell viability, and total protein released to the medium, were monitored and compared with the Met⁻ control. The results presented in FIG. 2 show that a significant proportion of the cells lost viability and released intracellular protein into the medium upon addition of methionine. These results strongly suggest that cells lose their integrity and lyse gradually after switching off the expression of SRB1/PSA1.

1.2.2 Repression of PKC1 Results in Intensive Cell Lysis

In order to test the applicability of the pMET3 regulation of PKC1, the recombinant plasmid pRS316-pMET3-PKC1 was transformed into a pkc1::LEU2 host (ZO124; Table 1). The transformants were able to grow without sorbitol in the absence of methionine, but were unable to grow when 2 mM methionine was added (data not shown). This indicated that pMET3 could be used for the regulation of the expression of PKC1. The strain ZO126, which carries a pMET3-regulated PKC1 gene, integrated at the homologous genomic site, was used in further experiments.

Figure 3:
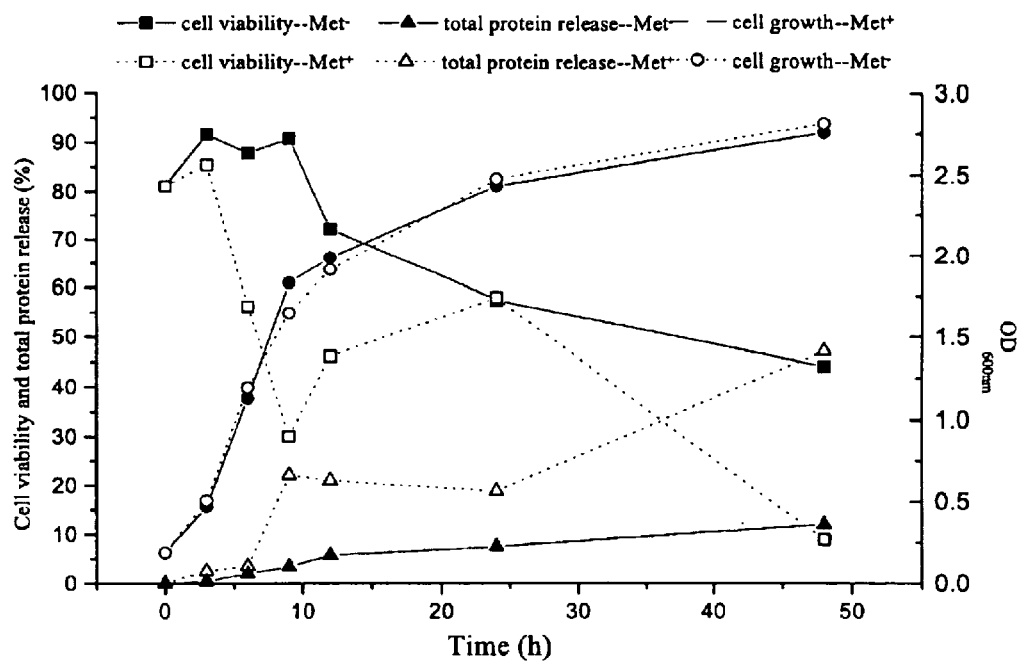

Strain ZO0126 was grown on minimal medium until early exponential phase and subjected to the standard procedure of methionine regulation as described in Materials and Methods. Cell viability and total protein release were monitored. The results (FIG. 3) demonstrate that, upon addition of methionine, cells grew another 1–2 generations and then started to lose viability very quickly. At the same time, yeast proteins were released in to the medium. After 48 h, of repression, some 45% of intracellular protein was detected in the growth medium, indicating extensive cell lysis. Remarkably, after 3–4 generations under repressive conditions, cell viability started to increase, followed by a gradual decrease. This indicates that some of the cells survived the initial shock and were able to grow for some time, perhaps aided by the lysis products of the dead cells, but subsequently succumbed to lysis.

Figure 4:
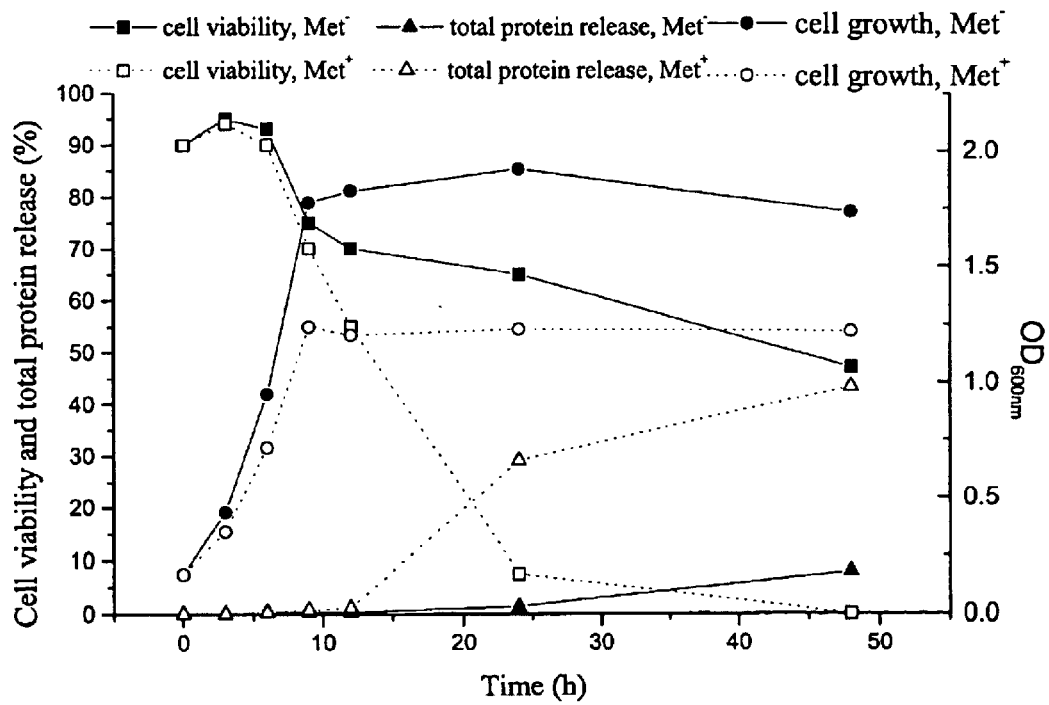
Figure 5:
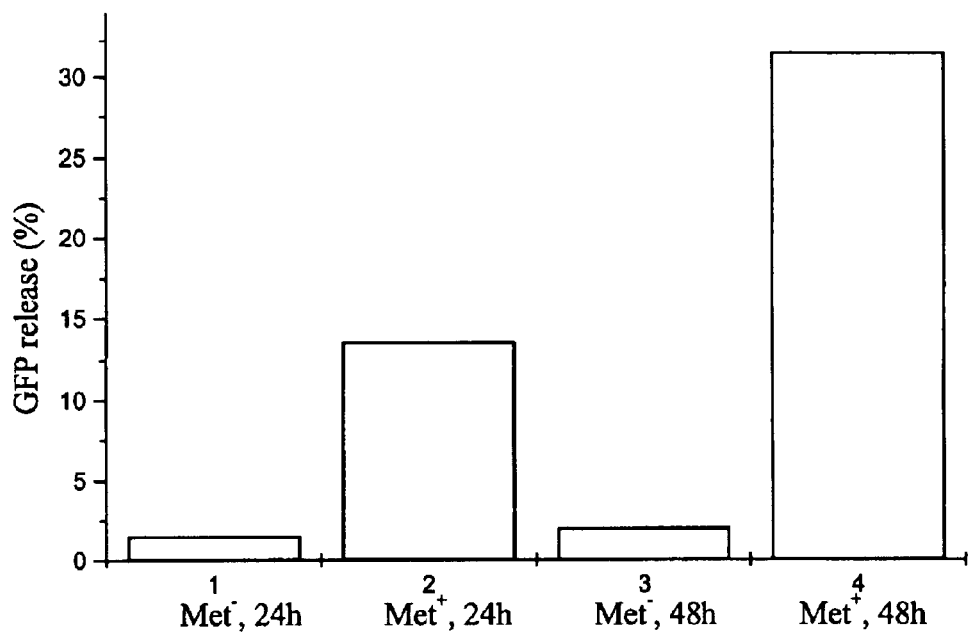

1.2.3 Concomitant Repression of SRB1/PSA1 and PKC1 Leads Rapidly to Extensive Cell Lysis Cells of strain ZO127, in which integrated copies of both SRB1/PSA1 and PKC1 are expressed from the MET3 promoter, were grown in minimal medium until early exponential phase, methionine was then added to repress this expression. The results (FIG. 4) show that, upon addition of methionine, cells lost viability more quickly than those having either of the single pMET3 expression cassettes (compare these results with those in FIGS. 2 and 3). Within 24 h, more than 80% of the cells lysed, releasing the bulk of their intracellular protein into the growth medium. These results indicate that the lysis phenotype conferred by the repression of SRB1/PSA1 and PKC1 is additive. Cells in which both SRB1/PSA1 and PKC1 expression may be regulated are particularly suited for use in the biotechnology industry in applications where inducible lysis is required 1.2.4 SRB1/PSA1 and PKC1-repressed Cells can Release an Heterologous Protein (GFP) from its Intracellular Location Green Fluorescent Protein (GFP), a heterologous protein, was used to demonstrate the applicability of cells in which repression of SRB1/PSA1 and PKC1 may be induced. For this purpose, the plasmid Pope-2μ (Walmsley et al., 1997 Yeast 13:1535–1545) was transformed into Z0127 and the transformants grown in selective medium. This 2μ-based plasmid expresses the coding sequence of jellyfish green fluorescent protein from the RAD54 promoter (Walmsley et al., 1997 supra). A methionine repression experiment was performed and GFP release measured. Little GFP was released into the medium by cells in the control (Met⁻) culture. However, more than 30% of cellular GFP was found in the medium of the experimental (Met⁺) culture, in which the expression of both SRB1/PSA1 and PKC1 was repressed for 48 h. (FIG. 5). This demonstrates that this lysis system is able to release both homologous and heterologous proteins from yeast cells.

1.3 Discussion

Compared with other cell lysis systems, where a temperature shift or the removal of an osmotic stabiliser is required, cells according to the first aspect of the invention may be induced to lyse according to the method of the second aspect of the invention by the addition of a simple chemical to repress the expression of two genes (SRB1/PSA1 and PKC1) involved in wall biogenesis to produce spontaneous cell lysis. Although the concentration of methionine used experimentally to repress the MET3 promoter was 2 mM, we have found it can be altered to achieve the same repressive effect (e.g. it may be lowered to 0.05–1.0 mM). A methionine analogue or cheaper metabolites in the methionine/threonine pathway may also be used as repressive agents for an industrial-scale process. An initial experiment has indicated that 0.2% yeast extract could suppress the cell growth of ZO125 (pMET3-SRB1) as well as 2 mM methionine, whereas 2% yeast extract could not suppress the cell growth of ZO126 (pMET3-PKC1) at all (data not shown).

EXAMPLE 2

During the studies performed in Example 1 it was surprisingly noticed that the new pattern of expression of SRB1/PSA1 and/or PKC1 from pMET3 resulted in changes in the flocculation phenotype of transformed cells. Further investigations were therefore performed which confirmed that such cells were useful according to the method of the third aspect of the present invention.

2.1. Materials and Methods 2.1.1 Strains and Media

The *Saccharomyces cerevisiae* strains used in this study, together with their genotypes and sources, are listed in Table 1 in Example 1 above. The strains were grown in minimal medium (SD) prepared according to Kaiser et al. (supra). Nutritional supplements were added to the medium as necessary.

2.1.2 Plasmids and Transformation

See Example 1.

2.1.3 Northern Analysis

Yeast total RNA was extracted and separated on a 1.5% (w/v) denaturing agarose gel according to the protocol described by Kaiser et al. (supra). Following blotting onto a nylon membrane (positively charged; Boehringer Mannheim), it was hybridised with the appropriated DNA probe labelled with $\alpha$-$^{32}$P-dCTP using a Rediprime™ kit (Amersham, UK). Prehybridisation, hybridisation, and washing steps were carried out following the procedure described by Engler-Blum et al. (Anal Biochem 210: p235–244, 1993). After washing, the membrane was wrapped in Saran-Wrap and exposed to a BioRad imaging screen (type BI) which was then developed with the BioRad phosphorimager (GS-363) and analysed with Molecular Analyser™ software.

2.1.4 Methionine Regulation of pMET3 Expression Cassettes

Cultures of strains containing pMET3-regulated cassettes were grown according to method 1.1.7.

2.1.5 Construction of Isogenic Wild-type Strain, ZO123

Used as the control in this study, a isogenic wild-type strain was constructed by transforming a PCR product containing the PKC1 gene into strain ZO124. The PKC1 coding sequence was PCR-amplified using YEplac195-PKC1 (see Example 1) as the template, a forward primer of sequence ID NO 1 and a reverse primer of sequence ID NO 2. Those transformants which could grow without 10% (w/v) sorbitol, but could not grow without a leucine supplement, were further checked for correct integration. This was done by diagnostic PCR, using one oligonucleotide of sequence ID NO 10, which anneals to PKC1 but not the deletant sequence and another of sequence ID NO 11, which anneals outside the PKC1 fragment. This gives a 0.85 kb fragment, as is the case with ZO123 (data not shown).

2.1.6 Construction of ZO125

ZO125 is based on ZO123 with pMET3-SRB1-LEU2 integrated at the chromosomal SRB1/PSA1 locus. SRB1.9e was digested with ApaI and BstI107I. The fragment containing the SRB1/PSA1 upstream region, pMET3-SRB1-LEU2 and SRB1/PSA1 downstream region was transformed into ZO0123. The correct integration was confirmed both phenotypically and by diagnostic PCR as previously used for FY23PSA1$^{MET3}$ (Table 1).

2.1.7 Flocculation Measurements

A cell culture (100 ml) was grown in SD medium containing 2% (w/v) glucose for 48 h. until stationary phase had been reached. A portion (50 ml) of this culture was placed in a 50 ml Falcon tube. Cells were collected by centrifugation at 5000 rpm for 5 min. The medium was poured away and cells were washed once with 250 mM EDTA and twice with sterile water before resuspension in water to a final concentration of 1–4×10$^9$ cells/ml. An aliquot (1 ml) of this suspension was used for quantification of flocculation as described by Stratford & Assinder (Yeast 7: 559–574, 1991).

Figure 7:
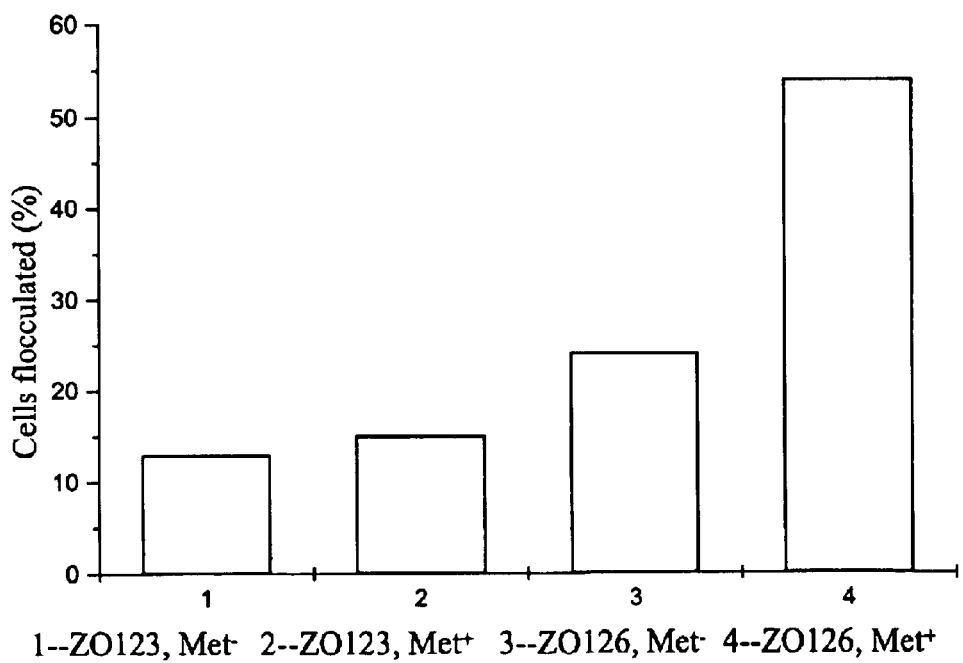
FIG. 7 is a bar chart illustrating the percentage of ZO123 and ZO126 cells flocculated in the absence or presence of methionine in Example 2.
Figure 6:
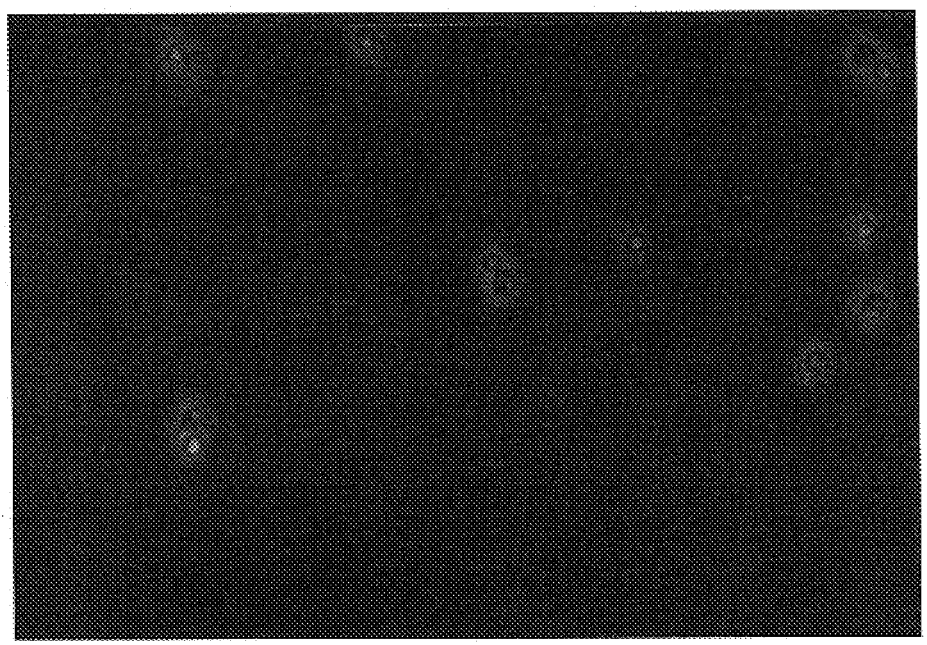
FIG. 6 is a photograph illustrating Flocs of ZO126 under expression conditions (Met$^-$, no methionine) and repression conditions (Met$^+$, 2 mM methionine) in Example 2.
Figure 6:
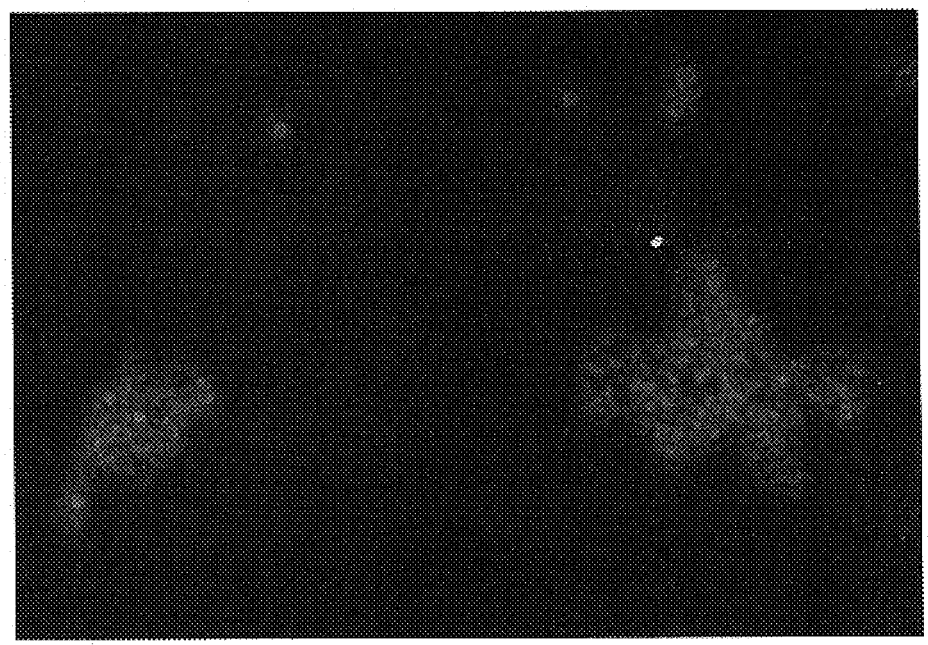

2.2 Results and Discussion 2.2.1 pMET3 Regulation of PKC1 Causes Flocculation Under Conditions of Methionine Repression Strain ZO126 (Table 1), carrying the pMET3-PKC1 cassette, was grown until early exponential phase when methionine (2 mM) was added to half of the culture in order to repress the expression of PKC1. Incubation was then continued at 30° C. for a further 48 h. The other half of the culture was grown for the same time in the absence of methionine. It was observed that flocs were formed in the stationary culture grown under repression condition (FIG. 6). Cells were harvested and flocculation was quantified as described in Materials and Methods. At the same time, the wild-type strain ZO123, grown under similar conditions, with and without methionine, was included as a control. The results (FIG. 7) show that the wild-type cells have very weak flocculation ability, irrespective of whether methionine was present or not. The flocculation ability of the strain in which PKC1 is under the control of pMET3: was about 50% higher than that of the wild type grown in medium without methionine. However, this strain showed at least a three to four times greater ability to flocculate when methionine was added to repress the expression PKC1.

Although we do not wish to be bound by any hypothesis, we believe repression of PKC1 can induce flocculation because it has been shown to be involved in glucan biosynthesis. Electron micrographs of the cell wall of a temperature-sensitive pkc1 mutant show that the wall loses its normal organisation at the restrictive temperature. At the permissive temperature, the wall consists of an inner transparent layer and an outer. dark-stained, mannoprotein layer. In contrast, at the restrictive temperature, the transparent layer almost completely disappears and the entire wall stains dark, suggesting that the inner (skeletal) layer of the wall has been affected. Thus upon addition of methionine to a ZO126 culture, cells are depleted of Pkc1p. We believe this is results in much thinner inner cell walls which render the mannose side-chains in the incorporated mannoprotein more accessible to flocculin and thereby lead to a higher ability for flocculation.

Figure 9:
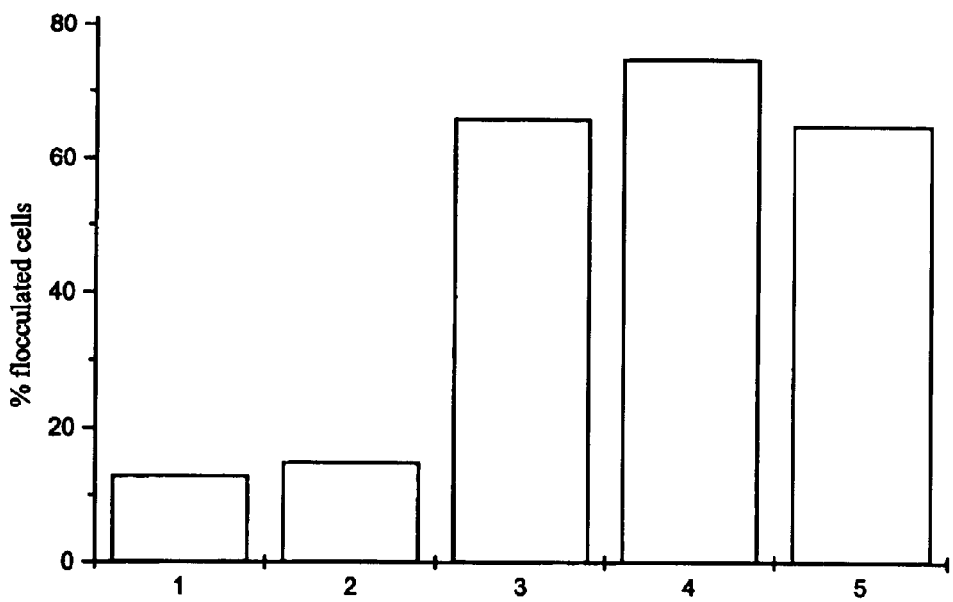
FIG. 9 is a bar chart illustrating the percentage of ZO123, ZO125 and ZO123/SRB1.9c cells flocculated in the absence or presence of methionine in Example 2.

2.2.2 Repression of SRB1/PSA1 Under the Control of the MET3 Promoter Causes Flocculation SRB1/PSA1 repression caused flocculation of ZO125. A flocculation test was performed on ZO125 cells which had been grown in permissive conditions until early exponential phase and then cultured for another 48 h in the presence of 2 mM methionine. The wild-type strain, ZO123, grown under the same conditions, was used as the control. As shown in FIG. 9, repression of SRB1/PSA1 in ZO125 leads to a 5-fold increase in flocculation.

Srb1p/Psa1p activity results in the production of GDP-mannose, an activated sugar that is involved, either directly or via the dolichol pathway, in all kinds of protein glycosylation, including GPI anchor synthesis. The product of the dominant flocculation determinant, FLO1, has been shown to be a GPI-anchored cell surface protein. Thus, it is conceivable that repression of SRB1/PSA1 results in a failure to incorporate Flo1p into the cell wall, or in its failure to function properly if incorporated. Mutants, like mnn9, that lack the outer polymannose chain on their mannoproteins grow slowly and display a clumpy morphology. Thus, the flocculation resulting from SRB1/PSA1 repression could be due to a profound change in cell-surface characteristics, including hydrophobicity.

Figure 8:
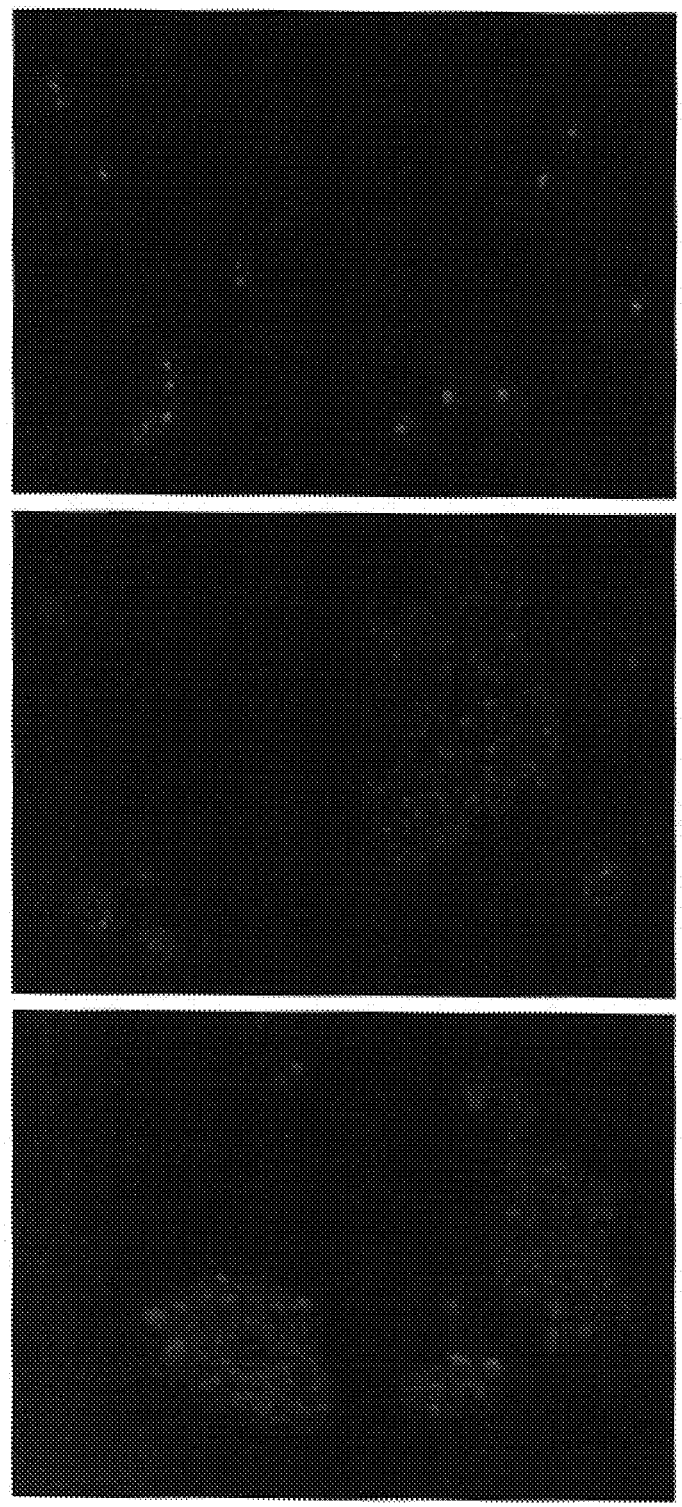
FIG. 8 is a photograph illustrating Flocs of ZO123 (a), ZO125 (b) and ZO123/SRB1.9e (c) grown under expression conditions (Met$^-$, no methionine) in Example 2.

2.2.3 Constitutive Expression of SRB1/PSA1 Under the Control of the MET3 Promoter Causes Flocculation at all Stages of the Batch Growth Cycle The growth of strain ZO125, harbouring the pMET3-SRB1 cassette, in SD medium under expression conditions (without methionine), was characterised by the following phenotypes. The culture was 'flaky' throughout batch growth. The flocculated cells at the exponential phase are shown in FIG. 8. This suggests that the expression of SRB1/PSA1 from pMET3, unlike that of PKC1 (above), leads to flocculation at any growth phase. ZO0125 cells grew faster, with a doubling time of 1.9 h. (while the doubling time of the wild-type strain ZO123 is 2.1 h.) and appeared to have bigger cell volumes (FIG. 8), in comparison to the wild-type isogenic control, ZO123. When the cells from both strains were grown to stationary phase and subjected to the flocculation test, it was observed (FIG. 9) that the cells carrying the pMET3-SRB1 expression cassette had a five times higher ability for flocculation than the control strain.

We also found that cells transformed with the pMET3-SRB1 cassette had a flocculating phenotype when grown in "permissive" media (i.e in the absence of methionine) (see FIGS. 8 and 9). This suggested to us that constitutive expression of SRB1/PSA1 under the regulation of pMET3 causes flocculation.

We further investigated how SRB1/PSA expression from the MET3 promoter caused flocculation by investigating whether pMET3-SRB1 led to flocculation in a wild-type strain. The plasmid SRB1.9e, which carries the pMET3-SRB1 cassette in a centromeric vector, was transformed into the wild-type strain ZO123, which has a wild-type copy of SRB1/PSA1 under the control of its own promoter. The transformants were grown in the same medium as that for ZO125, the strain containing an integrated copy of pMET3-SRB1 at the SRB1/PSA1 chromosomal locus. A flocculation phenotype, the same as that of ZO125, was observed in all growth phases and the cell volume appeared larger compared with that of the wild type (FIG. 8). The flocculation test, which was performed after the cells had been grown to stationary phase, showed that this transformant flocculates to the same degree as ZO125. This result confirmed that the flocculation phenotype caused when SRB1/PSA1 is transcribed from pMET3 is not due to the gene's underexpression but, rather, is the result of its constitutive expression.

The result of the viability test on FY23PSA1$^{MET3}$ shows that cell viability is not affected by the constitutive expression of SRB1/PSA1, suggesting that sufficient Srb1/Psa1p is synthesised under the control of pMET3 to allow yeast to go through its cell cycle. However, when SRB1/PSA1 is expressed from its own promoter, its transcription level increases some 4- to 6-fold at START. Thus the constitutive expression of SRB1/PSA1 from pMET3 would hyperactivate glycosylation at all other cell cycle phases; it may well be this that leads to enhanced cell growth and flocculation.

We have therefore established that the interaction between SRB1/PSA1 expression and the dominant flocculation genes is important in determining a flocculent phenotype and the repression of SRB1/PSA1 expression or the alteration of wildtype SRB1/PSA1 expression patterns (e.g. constitutive expression under the pMET promoter) can induce flocculation. Thus genetically modified yeasts in which SRB1/PSA1 expression is modulated may be used industrially according to the method of the fourth aspect of the invention to induce flocculation.

Flocculation provides a means of efficient separation of cells from the medium. However, most cell wall mutants with enhanced flocculation capacity are affected in cell growth or cell viability, like KRE6 and mnn9. The flocculation resulting from SRB1/PSA1 expression from the MET3 promoter has no overt effect on cell growth and viability. Thus cells in which SRB1 is under the regulation of an inducible promoter may be used industrially when flocculation only is required.

2.2.4 Flocculation Ability of a Double (pMET3-PSA1, pMET3-PKC1) Mutant

Figure 11:
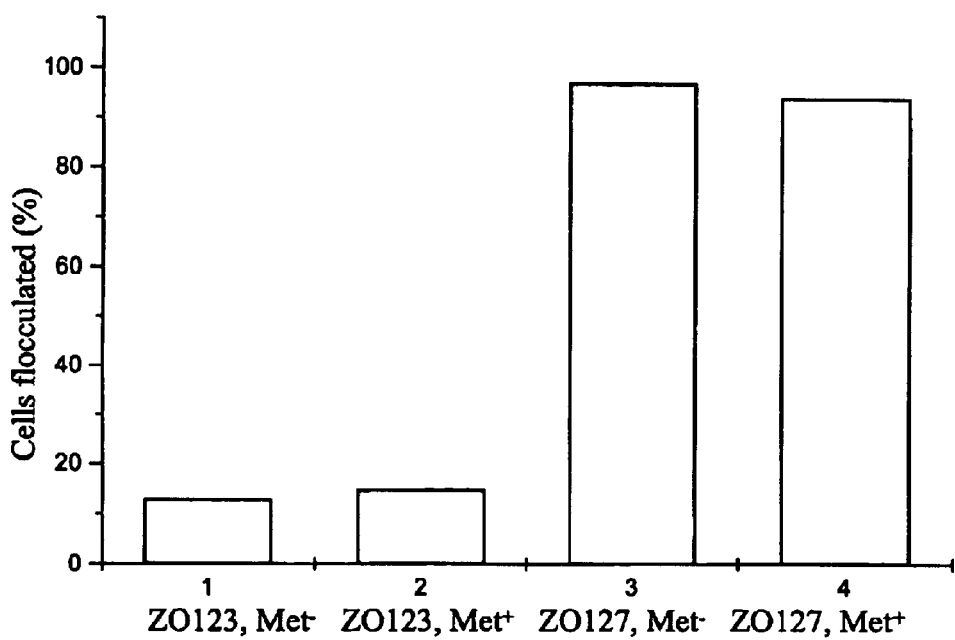
FIG. 11 is a bar chart illustrating the percentage of ZO123 and ZO127 cells flocculated in the absence or presence of methionine in Example 2.
Figure 10:
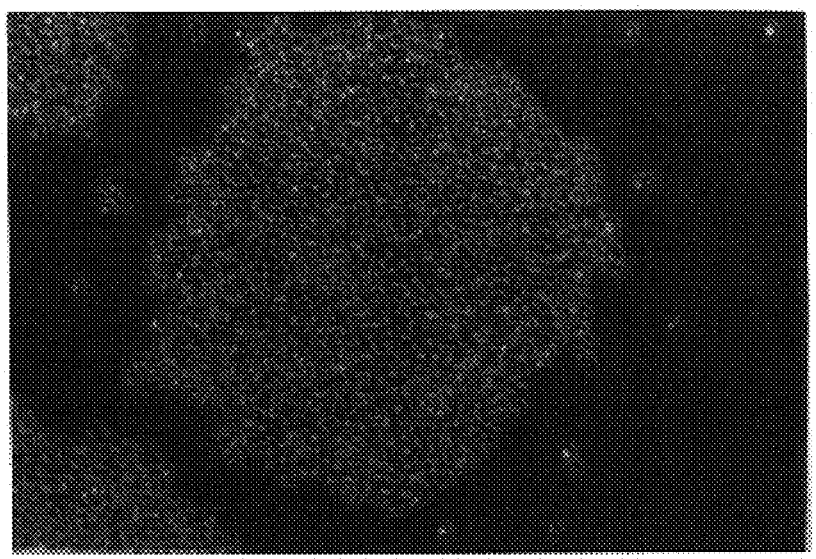
FIG. 10 is a photograph illustrating Flocs of ZO127 grown under expression conditions (Met⁻, no methionine) or repression (Met⁺, 2 mM methionine) in Example 2.
Figure 10:
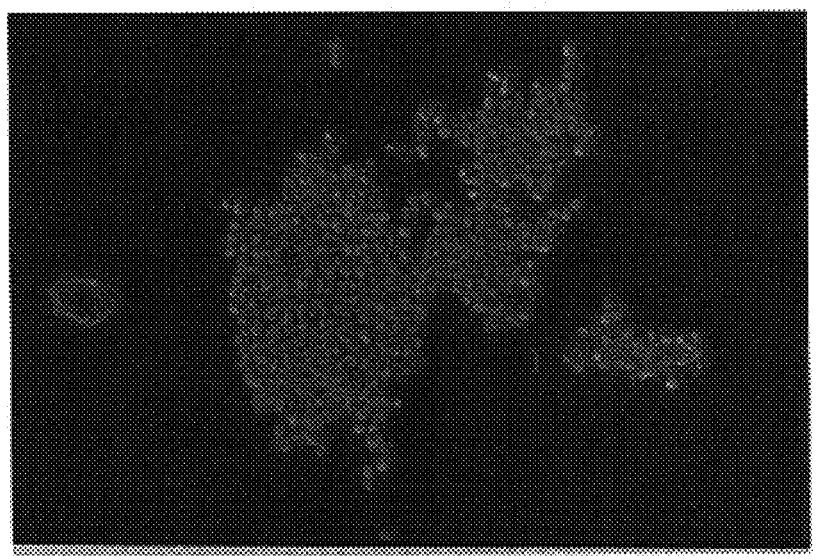

The strain ZO127 (see Table 1), carrying both the pMET3-PSA1 and pMET3-PKC1 cassettes, was used to test flocculation under non-repressing (Met$^-$) and repressing (Met$^+$) conditions. Under both conditions, cells from this strain formed very large flocs (FIG. 10) at all growth phases. After growth for 48 h, cells were harvested and subjected to a flocculation test (FIG. 11). Around 95% of the cells, from either the Met$^-$ or the Met$^+$ culture, formed large aggregates. This indicates that ZO127 cells have a higher ability for flocculation than those bearing the single cassettes (compare FIGS. 7, 9, and 11), suggesting that the flocculation effects resulting from pMET3-regulated PKC1 and SRB1/PSA1 expression or repression are additive.

Thus we have established that modulation of SRB1/PSA1 alone (see 2.2.3) or PKC1 and SRB1/PSA1 (2.2.4) is directly linked to flocculation. These results suggest that morphogenes in yeast must obey cell cycle controls whilst responding to environmental changes.

Concomitant repression of SRB1/PSA1 and PKC1 leads to extensive cell lysis and flocculation, making the system useful in heterologous protein expression and downstream operations in which controlled cell lysis and efficient separation of cell ghosts from the medium can be realised at the same time.

What is claimed is:

1. A yeast cell containing the PKC1 gene operatively linked to a heterologous inducible promoter and the SRB1/PSA1 gene operatively linked to a heterologous promoter.

2. A yeast cell containing the SRB1/PSA1 gene and the PKC1 gene each operatively linked to a heterologous inducible promoter.

3. The yeast cell according to claim 2 wherein the yeast cell is a strain of *Saccharomyces cerevisiae*.

4. The yeast cell according to claim 2 wherein the yeast cell is a strain of *Pichia pastoris, Hansenula polymorpha* or *Kluyveromyces lactis*.

5. The yeast cell according to claim 2 wherein at least one of the genes is operatively linked to a methionine regulated promoter.

6. The yeast cell according to claim 5 wherein the methionine regulated promoter is pMET3.

7. The yeast cell according to claim 6 wherein said PKC1 gene operatively linked to an inducible promoter is the PKC1 gene and operatively linked inducible promoter of the recombinant vector pRS316-pMET3-PKC1, pRS316-F$_1$F$_2$-pMET3-PKC1 or pRS316-F$_1$F$_2$-TRP1-pMET3-PKC1.

8. The yeast cell according to claim 6 wherein said SRB1/PSA1 gene operatively linked to an inducible promoter is the SRB1/PSA1 gene and operatively linked inducible promoter of the recombinant vector SRB1.9e.

9. The yeast cell according to claim 8 wherein said PKC1 gene operatively linked to an inducible promoter is the PKC1 gene and operatively linked inducible promoter of the recombinant vector pRS316-pMET3-PKC1, pRS316-$F_1F_2$-pMET3-PKC1 or pRS316-$F_1F_2$-TRP1-pMET3-PKC1.

10. A yeast cell containing the PKC1 gene operatively linked to a heterologous inducible promoter selected from the group consisting of:
   (i) a yeast strain having the genotype MATa his3 leu2 trp1 ura3 pkc1::LEU2, transformed with pRS316-pMET3-PKC1, pRS316-$F_1F_2$-pMET3-PKC1 or pRS316-$F_1F_2$-TRP1-pMET3-PKC1;
   (ii) a yeast strain having the genotype MATa his3 leu2 trp1 ura3, transformed with pRS316-pMET3-PKC1 or pMET3-PKC1 containing fragments of pRS316-$F_1F_2$-pMET3-PKC1 or pRS316-$F_1F_2$-TRP1-pMET3-PKC1; and
   (iii) a yeast strain having the genotype MATa his3 leu2 trp1 ura3 pkc1Δ:: TRP1-pMET3-PKC1.

11. A yeast cell according to claim 1 or 10 wherein the promoter or promoters is/are pMET3.

12. A method of regulating yeast cell lysis comprising:
   (i) growing yeast cells containing the SRB1/PSA1 gene and the PKC1 gene each operatively linked to an inducible promoter in a growth medium which activates the inducible promoter such that SRB1/PSA1 and PKC1 are expressed from said cells; and
   (ii) when lysis is required, growing the cells in a modified growth medium which represses SRB1/PSA1 and PKC1 expression such that cell lysis is induced.

13. The method according to claim 12 wherein the yeast cells contain the SRB1/PSA1 gene and the PKC1 gene each operatively linked to a heterologous inducible promoter.

14. The method according to claim 12 wherein the inducible promoter is pMET, the growth medium is methionine-free and the modified growth medium contains methionine.

15. The method according to claim 14 wherein the modified medium contains from between 0.05 mM and 20 mM methionine.

16. A method of isolating protein from yeast cells comprising growing cells and inducing lysis according to claim 12 and separating the protein released from the lysed yeast cells from yeast cell debris/ghosts.

17. The method according to claim 16 for isolating recombinant proteins expressed from genetically engineered yeast cells.

* * * * *

SEQUENCE LISTING

```
<160> NUMBER OF SEQ ID NOS: 14

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: PRIMER

<400> SEQUENCE: 1
gaaagcggcc gcaaaagtaa gtatagtatc ac                                    32

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: PRIMER

<400> SEQUENCE: 2
cctgagctcc aagataggta cgaacaaaa                                        29

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: PRIMER

<400> SEQUENCE: 3
ccgggtacca caagcagctg atgaaaagcc a                                     31
```

```
<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: PRIMER

<400> SEQUENCE: 4
acgcgtcgac aacctggagt gggacaaaca t                              31

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 5
catgcatgct aatataggaa gcatttaata                                30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: PRIMER

<400> SEQUENCE: 6
acgcgtcgac gcaagtgcac aaacaatact t                              31

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: PRIMER

<400> SEQUENCE: 7
attattctcc atgcgagcca gg                                        22

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: PRIMER

<400> SEQUENCE: 8
catgctgcct atgttgca                                             18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 9
acgacagaga gagacccaag                                           20

<210> SEQ ID NO 10
<211> LENGTH: 22
<212> TYPE: DNA
<213> ORGANISM: Artificial Sequence
<220> FEATURE:
```

-continued

```
<223> OTHER INFORMATION: Description of Artificial Sequence: PRIMER

<400> SEQUENCE: 10
tgtcgattgg tgggcatttg gg                                          22

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: PRIMER

<400> SEQUENCE: 11
cgtcatgaac tctcgcggat ttgata                                      26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 12
cgcggatcca gccacaagac aagctacaac                                  30

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: PRIMER

<400> SEQUENCE: 13
actagcatgc aatactacag acattgatag ccaa                             34

<210> SEQ ID NO 14
<211> LENGTH: 304
<212> TYPE: DNA
<213> ORGANISM: Saccharomyces sp.
<220> FEATURE:
<223> OTHER INFORMATION: Description of Unknown Organism: YEAST

<400> SEQUENCE: 14
acaagcagct gatgaaaagc caagacataa gtattgttgc ccacactgtg ggtcttcatt    60
tccaagatgt gccatatgtc tcatgcctct aggaacgtca aacttacctt ttgtaataaa   120
tgggacgcaa tcacgcgatc aatgcagaca gaagactctc aagatggtgc aaatcgcgaa   180
ctcgtaagta gaaaactgaa gttgaacgag tggttcagct tctgtttgag ttgcaaccat   240
ggtatgcatg ccggtcacgc tgaagaatgg tttgacagac ataatgtttg tcccactcca   300
ggtt                                                              304
```